(12) United States Patent
Uchiyama et al.

(10) Patent No.: US 7,419,470 B2
(45) Date of Patent: Sep. 2, 2008

(54) METHOD AND DEVICE FOR MEASURING INTRAOCULAR TENSION

(75) Inventors: Akihiko Uchiyama, Yokohama (JP); Kenji Yanashima, Ichikawa (JP); Sunao Takeda, Ichikawa (JP); Go Taguchi, Tokyo (JP); Takuro Yokoyama, Tokyo (JP)

(73) Assignees: Waseda University, Totsuka-cho, Shinjuku-ku, Tokyo (JP); Kowa Company, Ltd., Nishiki 3-chome, Naka-ku, Nagoya-shi, Aichi (JP)

( * ) Notice: Subject to any disclaimer, the term of this patent is extended or adjusted under 35 U.S.C. 154(b) by 557 days.

(21) Appl. No.: 10/473,108

(22) PCT Filed: Mar. 29, 2002

(86) PCT No.: PCT/JP02/03180

§ 371 (c)(1),
(2), (4) Date: Sep. 29, 2003

(87) PCT Pub. No.: WO02/078531

PCT Pub. Date: Oct. 10, 2002

(65) Prior Publication Data

US 2004/0097799 A1    May 20, 2004

(30) Foreign Application Priority Data

Mar. 30, 2001 (JP) ............................. 2001-101590

(51) Int. Cl.
*A61B 8/00* (2006.01)
*A61B 8/12* (2006.01)
*A61B 8/14* (2006.01)

(52) U.S. Cl. ..................................... 600/438; 600/437

(58) Field of Classification Search ................. 600/437, 600/438, 552; 601/2
See application file for complete search history.

(56) References Cited

U.S. PATENT DOCUMENTS 3,070,087 A    12/1962    Sittel (Continued)

FOREIGN PATENT DOCUMENTS

JP    02-180241    7/1990

(Continued)

OTHER PUBLICATIONS

Alam, et al. "Detection of Intraocular Pressure Change in a Human Eye Model Using Sonoelastic Doppler Ultrasound," Paper presented at 1992 Ultrasonics Symposium.

(Continued)

*Primary Examiner*—Brian L. Casler
*Assistant Examiner*—James Kish
(74) *Attorney, Agent, or Firm*—Knobbe Martens Olson & Baer LLP (57) ABSTRACT

An intraocular tension measuring method comprising vibrating an eyeball to be examined by a sound wave, measuring vibration of the eyeball to be examined by a noninvasive means to determine a Q value of resonance of the eyeball to be examined, and calculating intraocular tension from the Q value, and an intraocular tension measuring device comprising a vibrating means for vibrating an eyeball to be examined by a sound wave, a measuring means for noninvasively measuring vibration of the eyeball to be examined, a Q value calculating means for calculating a Q value of resonance of the eyeball to be examined from the vibration measured by the measuring means, and an intraocular tension calculating means for calculating intraocular tension from the Q value.

5 Claims, 6 Drawing Sheets

U.S. PATENT DOCUMENTS

| | | | |
|---|---|---|---|
| 3,192,765 A * | 7/1965 | Keiper | 600/398 |
| 3,882,718 A | 5/1975 | Kriebel | |
| 3,948,248 A * | 4/1976 | Zuckerman et al. | 600/457 |
| 4,930,507 A * | 6/1990 | Krasnicki et al. | 600/402 |
| 4,945,913 A | 8/1990 | Krasnicki et al. | |
| 5,251,627 A * | 10/1993 | Morris | 600/398 |
| 5,349,955 A | 9/1994 | Suzuki | |
| 5,375,595 A | 12/1994 | Sinha et al. | |
| 6,085,594 A | 7/2000 | Gutierrez et al. | |

FOREIGN PATENT DOCUMENTS

| | | |
|---|---|---|
| JP | 04-208129 | 7/1992 |
| JP | 05-253190 | 10/1993 |
| JP | 06038930 A2 | 2/1994 |
| JP | 06-213749 | 8/1994 |
| JP | 08280630 A2 | 10/1996 |
| JP | 08-322803 | 12/1996 |
| JP | 09-103411 | 4/1997 |
| JP | 10-293077 | 11/1998 |
| RU | 2102917 C1 | 1/1998 |
| SU | 1823788 A3 | 6/1993 |
| WO | WO 94/23642 | 10/1994 |
| WO | WO 95/04495 | 2/1995 |
| WO | WO 98/49934 | 11/1998 |
| WO | WO 01/15594 A1 | 3/2001 |

OTHER PUBLICATIONS

Supplementary European Search Report from corresponding European application serial No. EP 02 70 7255.

* cited by examiner

METHOD AND DEVICE FOR MEASURING INTRAOCULAR TENSION

RELATED APPLICATIONS

This application is the U.S. National Phase under 35 U.S.C. § 371 of International Application PCT/JP02/03180, filed Mar. 29, 2002, which was published in a language other than English which claims priority of JP 2001-101590, filed Mar. 30, 2001 Each of the above applications are incorporated herein by reference in their entirety.

TECHNICAL FIELD

The present invention relates to an intraocular tension measuring method and an intraocular tension measuring device.

BACKGROUND ART

The following methods are generally known as intraocular tension measuring methods: a method of applying a predetermined pressure to a cornea and monitoring a depression of the cornea at this time, thereby measuring intraocular tension; and a method of, by making a presser in contact with the cornea or by blowing air to the cornea, measuring a tension when a portion of the cornea becomes flat, thereby measuring intraocular tension. With those methods, it is necessary to ensure high safety because the cornea is directly stimulated. Accordingly, it is required that an examiner is a doctor or a health professional. In addition, a load on a person when examined is large because local anesthesia is required or air blowing causes discomfort.

Regarding such problems, several kinds of methods were proposed: a method of vibrating the surface of an eyeball by a sound wave and measuring intraocular tension based on an amplitude of the vibration, a resonance frequency of the eyeball, or a velocity of a surface wave of the eyeball (JP 02-181241A, U.S. Pat. No. 5,375,595, and U.S. Pat. No. 5,251,627); a method of pressing down an eyelid in a closed-eye state to measure intraocular tension (JP 06-105811 A, JP 08-280630 A, and JP 08-322803 A); and the like.

On the other hand, in a method of measuring an intracranial pressure using a sound wave, a Q value is known as one of the parameters related to the intracranial pressure (U.S. Pat. No. 5,919,144).

DISCLOSURE OF THE INVENTION

An object of the present invention is to provide an intraocular tension measuring method and an intraocular tension measuring device, which are safe and have small errors.

The present inventors found that the Q value in resonance at the time when the eyeball is vibrated is related to intraocular tension and the relation is not influenced by the size of the eyeball, and this has led to the present invention.

Therefore, the present invention provides the following methods and devices.

(1) An intraocular tension measuring method comprising vibrating an eyeball to be examined by a sound wave, measuring vibration of the eyeball to be examined by a noninvasive means to determine a Q value of resonance of the eyeball to be examined, and calculating intraocular tension from the Q value.

(2) An intraocular tension measuring device comprising a vibrating means for vibrating an eyeball to be examined by a sound wave, a measuring means for noninvasively measuring vibration of the eyeball to be examined, a Q value calculating means for calculating a Q value of resonance of the eyeball to be examined from the vibration measured by the measuring means, and an intraocular tension calculating means for calculating intraocular tension from the Q value.

BEST MODES FOR CARRYING OUT THE INVENTION

Hereinafter, the method of the present invention and the device of the present invention will be described in order.

<1> Method of the Present Invention

The method of the present invention is an intraocular tension measuring method, characterized by comprising vibrating an eyeball to be examined by a sound wave, measuring vibration of the eyeball to be examined by a noninvasive means to determine a Q value of resonance of the eyeball to be examined, and calculating intraocular tension from the Q value.

With respect to the measurement of a Q value in resonance of an eyeball to be examined, the eyeball to be examined is vibrated by a sound wave and the vibration is measured by a noninvasive means. The entire eyeball to be examined may be vibrated or a portion of a sclera may be vibrated. When the sound wave is used, the eyeball to be examined can be vibrated without being in direct contact with a cornea. In addition, even in the case of a closed-eye state, the eyeball to be examined can be vibrated. In other words, an eyelid as a body tissue can be acoustically regarded as water which is suitable as a medium of a sound pressure. Accordingly, the eyelid does not hinder the vibration of the eyeball resulting from the sound wave. A frequency of the sound wave to be used is appropriately selected according to the Q value calculating method.

The calculation of the Q value from the measured vibration can be conducted by, for example, a frequency method or an impulse method. According to the frequency method, a frequency to be used may be continuously or discretely changed within an arbitrary range including a frequency at which the eyeball to be examined resonates (resonance point). According to the impulse method, the sound wave is used as a pulse and the pulse to be used includes the frequency component higher than the resonance point. In addition, the impulse method may include an S/N ratio improving step such as averaging of results of the measurements that have been repeatedly conducted.

Alternatively, approximate Q may be obtained from the calculation different from that of Q defined in the circuit theory, for example, a ratio between a gain at the resonance point and a gain at a frequency apart from the resonance point by a given frequency. In addition, the Q value may be determined from a ratio of gains at two frequencies.

The vibration produced by the sound wave is generally the vibration of a sine wave or a substantial sine wave, and the vibration of a sine wave is preferable.

A sound wave generating source is not particularly limited. For example, a speaker, an earphone, or the like can be used. A vibration measuring means is not particularly limited if it is not in direct contact with the eyeball. However, it is preferable that a sound wave resulting from the vibration of the eyeball to be examined is measured. As a sound wave measuring means, a microphone (including an electret condenser), a noncontact displacement meter, an acceleration sensor, and the like can be used. When the sound wave generating source and the vibration measuring means are located close to each other, it is preferable that the sound wave generating source and the vibration measuring means are selected such that one is not influenced by the other.

In this specification, "a noninvasive means" indicates a means that is not in direct contact with the cornea. With respect to the noninvasive means for measuring the vibration of the eyeball to be examined, there are a means for measuring the sound wave resulting from the vibration of the eyeball, a means for optically measuring a displacement of the surface of the eyeball, and the like.

It is preferable that the measurement of the vibration of the eyeball is conducted by measuring the sound wave resulting from the vibration. In this case, as described above, the eyelid can be acoustically regarded as water which is suitable as a medium of a sound pressure. Therefore, the influence of the eyelid on a resonance characteristic is small, so that the vibration of the eyeball to be examined can be measured even in a closed-eye state.

The calculation of intraocular tension based on the Q value can be conducted in a manner in which a relationship between the intraocular tension and the Q value is obtained by measuring a Q value of an eyeball whose intraocular tension is already known, and the measured Q value is converted into intraocular tension based on the relationship. Because the relationship between the intraocular tension and the Q value is not influenced by the size of the eyeball, it is unnecessary to conduct correction according to the size of the eyeball. In other words, the intraocular tension can be accurately measured without being influenced by individual differences in the size of the eyeball.

<2> Device of the Present Invention

The device of the present invention is an intraocular tension measuring device, characterized by comprising a vibrating means for vibrating an eyeball to be examined by a sound wave, a measuring means for noninvasively measuring vibration of the eyeball to be examined, a Q value calculating means for calculating a Q value of resonance of the eyeball to be examined from the vibration measured by the measuring means, and an intraocular tension calculating means for calculating intraocular tension from the Q value.

The vibrating means can vibrate the eyeball to be examined by the sound wave. Such vibrating means generally emits a sound wave having a variable frequency and is composed of, for example, a frequency variable type oscillator and a transmitting element which is connected with the oscillator and transmit a sound wave according to the signal from the oscillator. As examples of the transmitting element, a conductive type or piezoelectric type speaker, a conductive type or piezoelectric type earphone, and the like can be given. The vibration produced by the sound wave is generally the vibration of a sine wave or a substantial sine wave, preferably, the sine wave or the sum of sine waves.

The measuring means noninvasively measures the vibration of the eyeball to be examined. Note that in this specification, a word "noninvasively" indicates that a member that is in direct contact with the cornea is not used. Such a measuring means is composed of, for example, a receiving element for measuring the sound wave resulting from the vibration of the eyeball to be examined and an amplifying circuit for amplifying a signal from the receiving element. As examples of the receiving element, a condenser microphone and the like can be given.

The Q value calculating means calculates the Q value of resonance of the eyeball to be examined from the vibration measured by the measuring means. For example, there is a means for calculating the Q value based on a transfer characteristic obtained by measuring the vibration of the eyeball to be examined when the frequency of the sound wave is changed within the range including the resonance frequency of the eyeball to be examined. Such Q value calculating means is composed of, for example, a computer for calculating the Q value from the frequency of the sound wave inputted from the vibrating means and the vibration inputted from the measuring means.

A filter for cutting off an unnecessary signal may be provided between the measuring means and the Q value calculating means.

Figure 1:
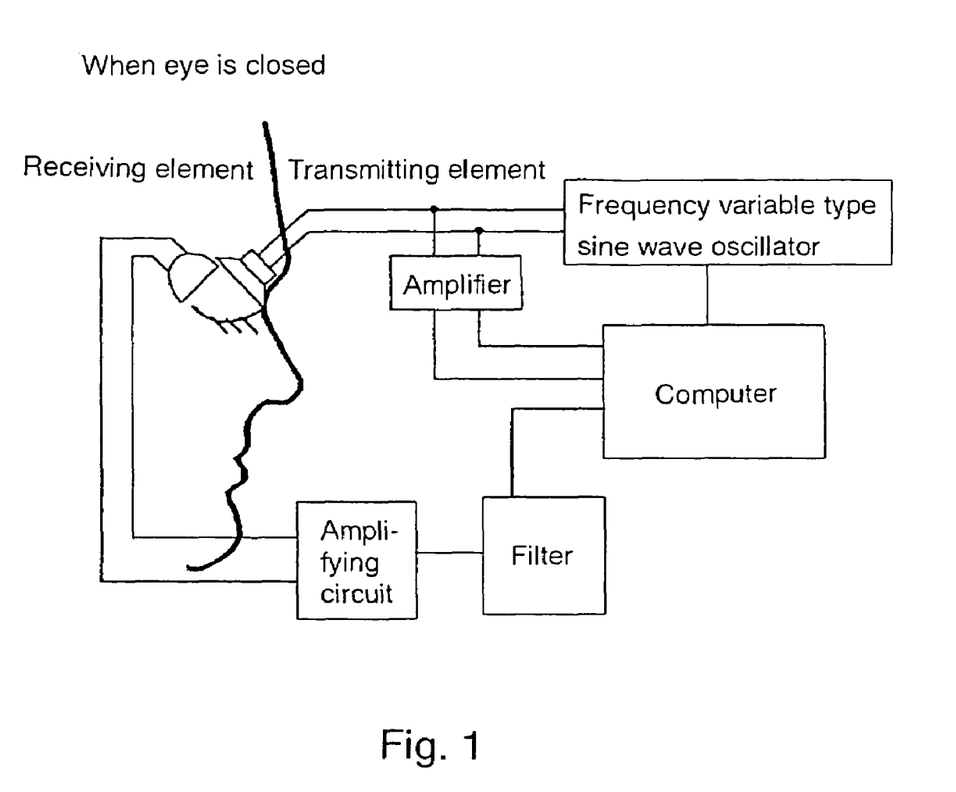
FIG. 1 is an entire structural diagram showing an example of a device of the present invention.

An embodiment of the device of the present invention will be described with reference to FIG. 1. A transmitting element is connected with a frequency variable type sine wave oscillator. A sound wave is emitted from the transmitting element according to an oscillation signal outputted from the oscillator. In addition, the oscillation signal from the frequency variable type sine wave oscillator is inputted to a computer through an amplifier. A receiving element is connected with an amplifying circuit. A signal from the receiving element is amplified by the amplifying circuit and inputted to the computer through a filter. The transmitting element and the receiving element are located at different positions on an eyelid.

According to this embodiment, the frequency variable type sine wave oscillator and the transmitting element connected with the oscillator constitute the vibrating means. The receiving element and the amplifying circuit that amplifies the signal from the receiving element constitute the measuring means. The computer constitutes the Q value calculating means.

The measurement of the intraocular tension using the device of this embodiment can be conducted as follows, for example. (1) Locate sound wave transmitting and receiving elements on an eye. (2) Transmit a sound wave from the transmitting element to the eye. (3) Change the frequency of the sound wave to be transmitted, and determine transfer frequency characteristics of transmission and reception. (4) Determine the Q value of the resonance frequency from the obtained transfer frequency characteristics. (5) Determine intraocular tension corresponding to the determined Q value.

The vibrating means and the measuring means are generally provided in a device main body in such a manner that the vibration of the vibrating means is not directly transferred to the measuring means. It is preferable that the device further has a means capable of making the vibrating means and the measuring means in contact with the eyelid of the eyeball to be examined by an adequate pressure. The vibrating means and the measuring means may be provided on a flexible material to be attached to the main body.

An optimum condition for the measurement is the condition in which the eyelid is slightly deformed in regions that are in contact with the transmitting element and the receiving element, the transmitting element and the receiving element are in close contact with the eyeball through the eyelid, and the eyeball is kept in a natural state in which it is not deformed. Accordingly, pressures at which the transmitting element and the receiving element are pressed against the eyeball are adjusted so as to obtain such a condition.

EXAMPLES

Hereinafter, the present invention will be described with reference to Examples. However, the present invention is not limited to those.

Example 1

Figure 2:
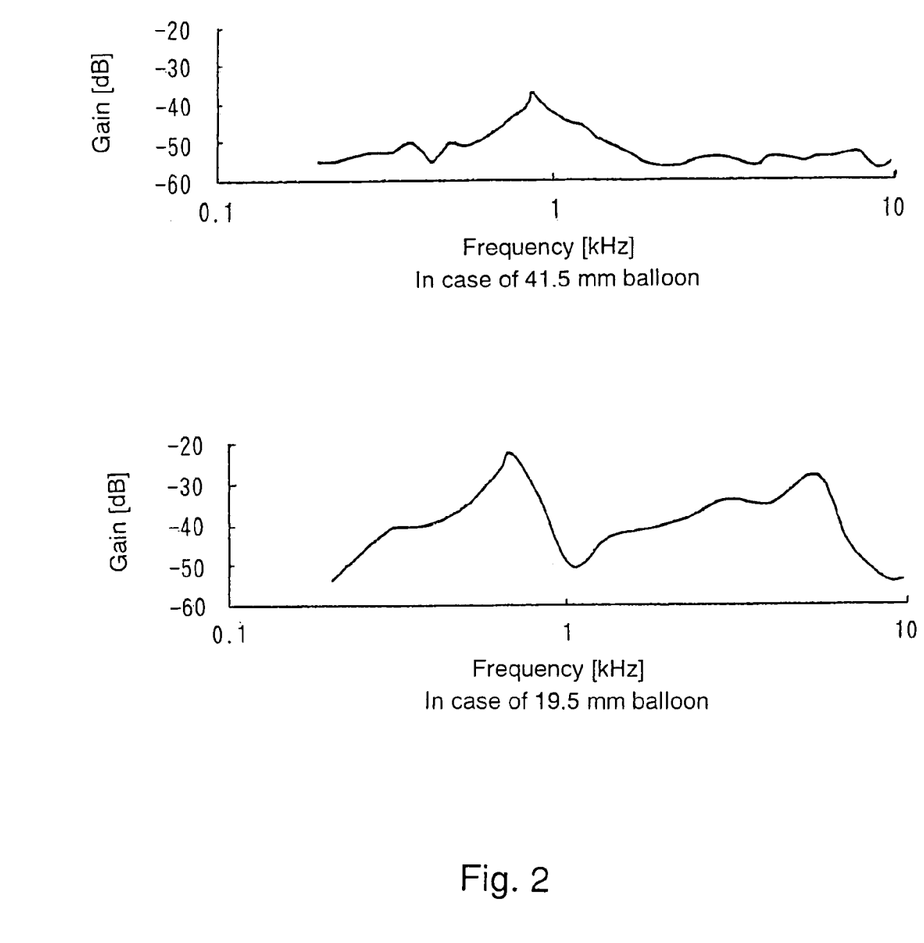
FIG. 2 shows examples of results obtained by measuring a transfer characteristic.

A balloon filled with water so as to obtain a predetermined inner pressure was used as a model of an eyeball. An earphone as a transmitting element and a microphone as a receiving element were attached to the balloon and a transfer characteristic was measured. FIG. 2 shows measured waveforms. In the measured waveforms, a difference of gain between a frequency in a peak and a low frequency sufficiently apart from the peak corresponds to a Q value. As is apparent from FIG. 2, it is found that, even if the diameter of the balloon is changed, the difference of gain is not substantially changed, which means the Q value is not influenced by the size of the balloon. Therefore, when intraocular tension is obtained from the Q value, it is considered unnecessary to take into account individual differences in the size of the eyeball.

Example 2

A transfer characteristic was measured using the eyeball of a pig (pig's eye) and a relationship between intraocular tension and a Q value was obtained from a measured waveform.

An earphone as a transmitting element and a condenser microphone as a receiving element were respectively inserted into a rubber vibration isolator in which holes were provided. The rubber vibration isolator was attached to a base made from corrugated cardboard. The pig's eye was placed on the base such that the earphone was in contact with the pupil (black portion) and the condenser microphone was in contact with the white portion. The pig's eye was just placed on the base and the transmitting and receiving elements were not fixed thereto by an adhesive or a two-sided tape.

The pig's eye was stuck from an optic nerve with an injection needle. The injection needle was connected with a container that held a physiological salt solution. The height of the water surface of the container was made substantially equal to the position of the pig's eye, and the pressure of the inner portion of the pig's eye was changed by vertically moving the container.

Figure 3:
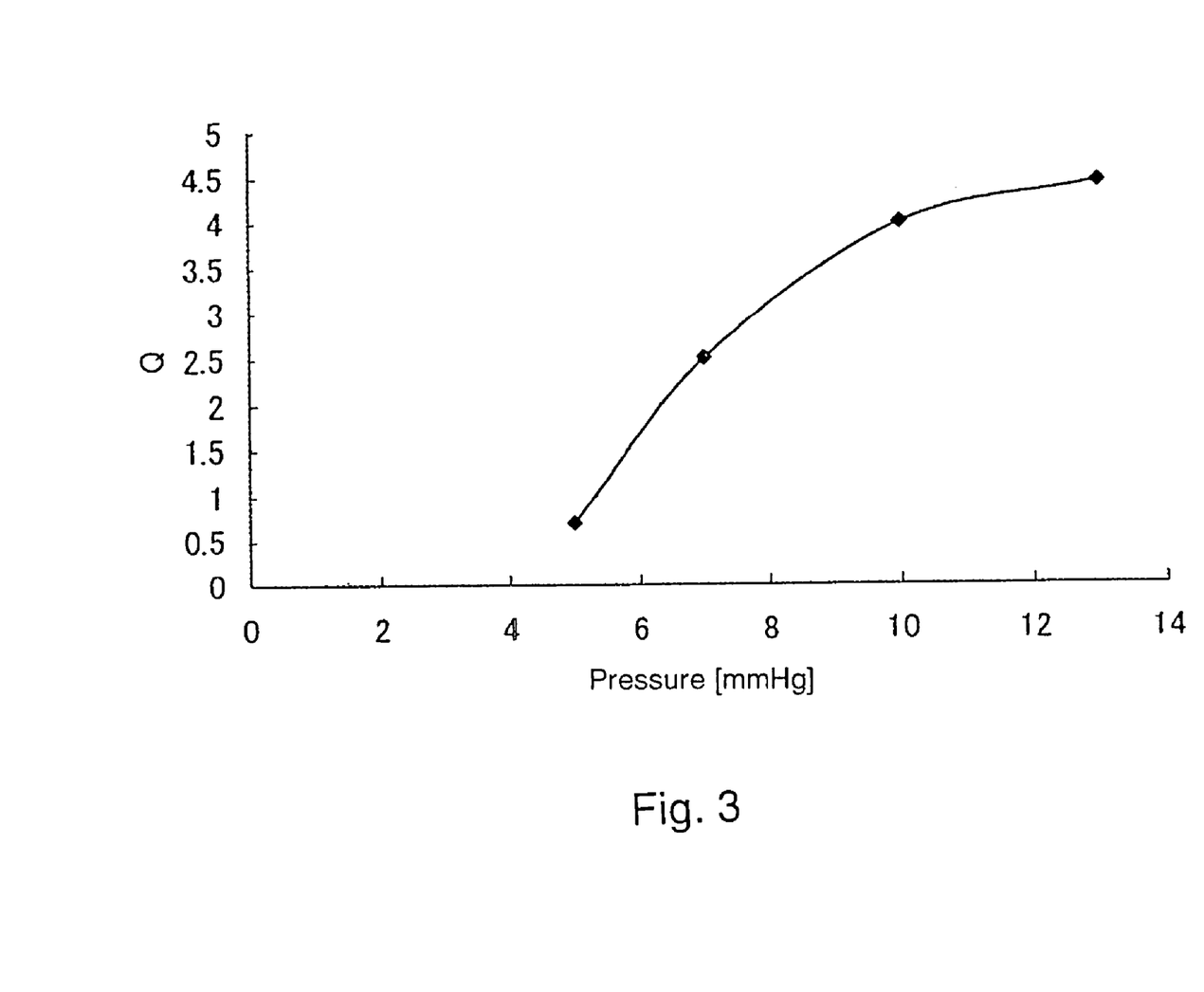
FIG. 3 shows an example of a relationship between intraocular tension and a Q value.

FIG. 3 shows the results indicating the relationship between the intraocular tension and the Q value, which was obtained. As is apparent from FIG. 3, it is found that the Q value is changed depending on the intraocular tension.

Example 3

Figure 4:
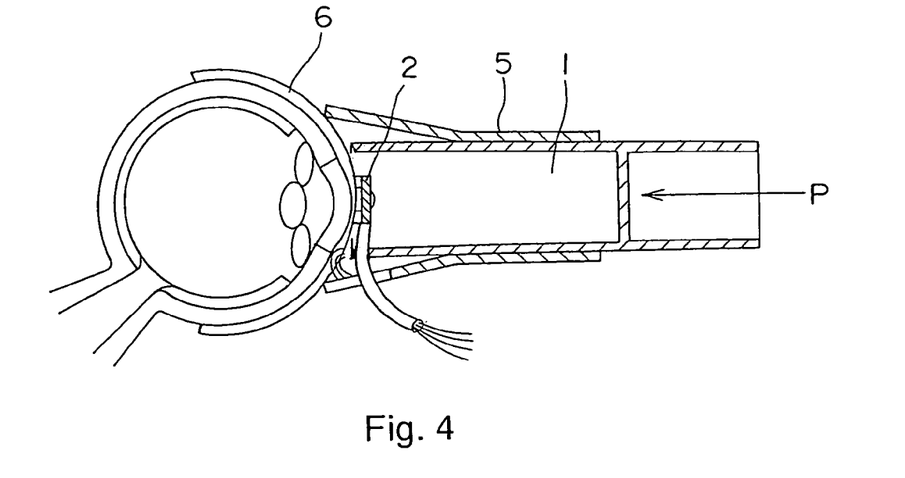
FIG. 4 is a side sectional view of a device of Example 3.
Figure 5:
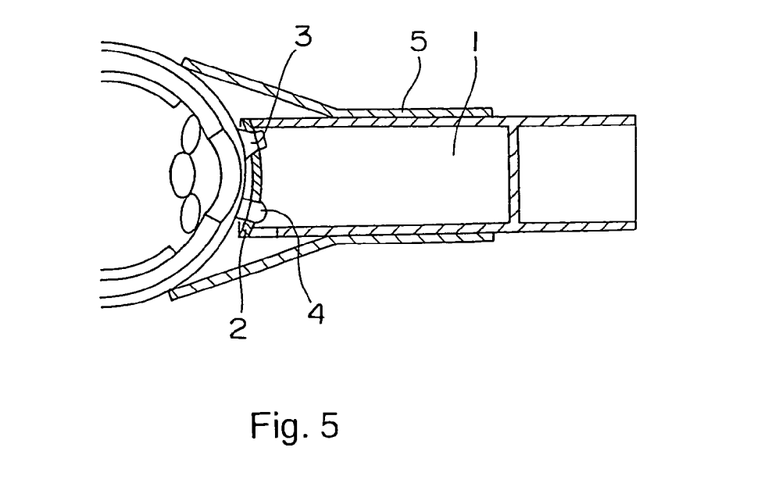
FIG. 5 is a top sectional view of the device of Example 3.
Figure 6:
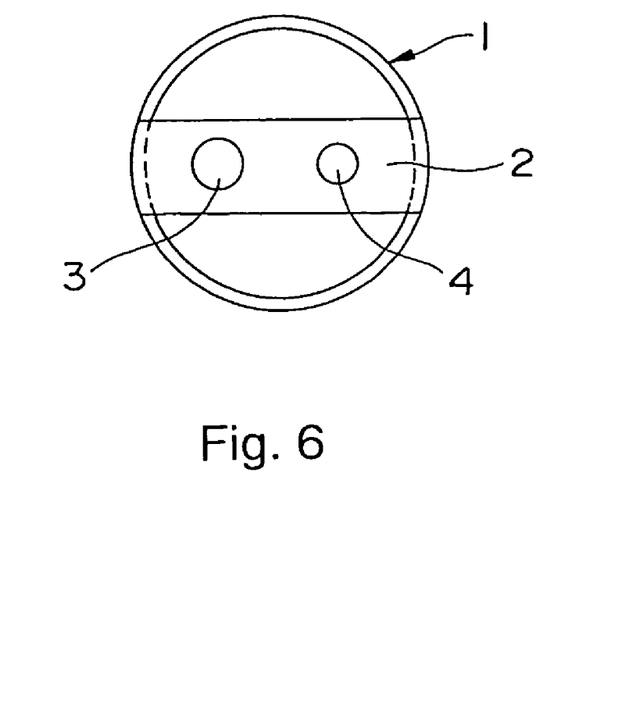
FIG. 6 is a front view of the device of Example 3.

A Q value was measured for a human eyeball. In this example, a device as shown in FIGS. 4 to 6 was used. FIG. 4 is a side sectional view, FIG. 5 is a top sectional view, and FIG. 6 is a front view. The device has the following characteristics.

Figure 7:
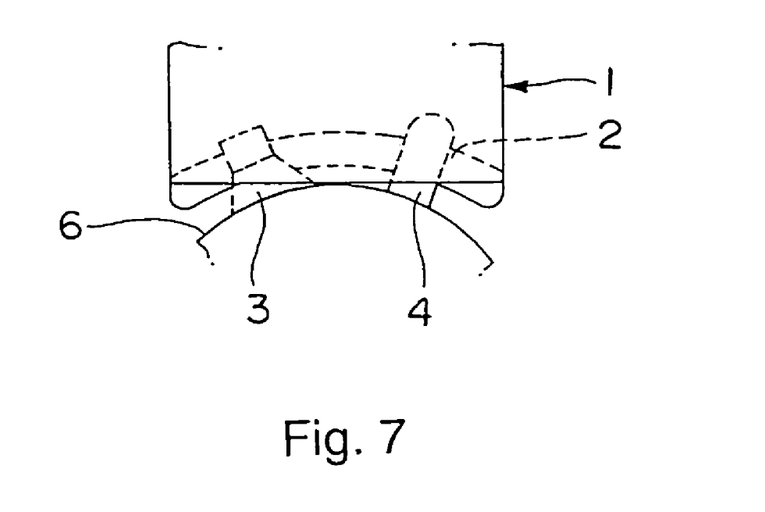
FIG. 7 is an explanatory view showing a state at the time when the device of Example 3 is pressed down on an eyeball.

1. An earphone as a transmitting element 3 and a condenser microphone as a receiving element 4 are respectively inserted into a rubber vibration isolator 2 in which holes are provided. The rubber vibration isolator 2 is attached to a cylindrical main body 1 having an isolation wall in a substantially central portion. The main body 1 is inserted into a holder 5. Because the rubber vibration isolator 2 is located between the transmitting element 3 and the receiving element 4, there is no case of direct transmit of vibrations from the transmitting element 3 to the receiving element 4. In addition, the rubber vibration isolator 2 is bent, so that the transmitting element 3 and the receiving element 4 are in contact with an eyelid 6 in a direction substantially vertical thereto (FIG. 7).

2. One end of the holder 5 is widened, so that it can be put on the face of a person to be examined without touching an eye to be examined. In addition, the holder 5 is hollowed, so that the main body 1 can be moved in the axis direction of the holder 5. Accordingly, the main body can be made in close contact with the eye to be examined through the eyelid 6 by an adequate pressure P and the eye to be examined can be covered. Thus, the influences of air present between the elements and the eyelid, sound and vibration from the outside, and the like, can be prevented, so that accurate measurement is possible.

A pressing means such as a spring may be used for a method of applying the pressure P. In this example, the eye to be examined was faced upward, pressing was made by placing a coin on the isolation wall of the main body 1. According to this method, P can be finely adjusted.

When P is too strong, the degree of freedom of the eyeball is lost. Accordingly, even if the eyeball receives a sound wave from the transmitting element 3, it cannot vibrate in a natural state. Therefore, accurate measurement of intraocular tension is impossible. On the other hand, when P is too weak, a space is caused between the transmitting element 3 and the eyelid 6, and between the receiving element 4 and the eyelid 6, and the necessary transfer of vibration (sound wave) from the transmitting element 3 to the eyeball is hindered by air present therein. Therefore, accurate measurement of intraocular tension is impossible.

An optimum condition for the measurement is the condition in which the eyelid 6 is slightly deformed, the transmitting element 3 and the receiving element 4 are in close contact with the eyeball through the eyelid 6, and the eyeball is kept in a natural state in which it is not deformed. Therefore, P was adjusted so as to obtain such a condition.

Figure 8:
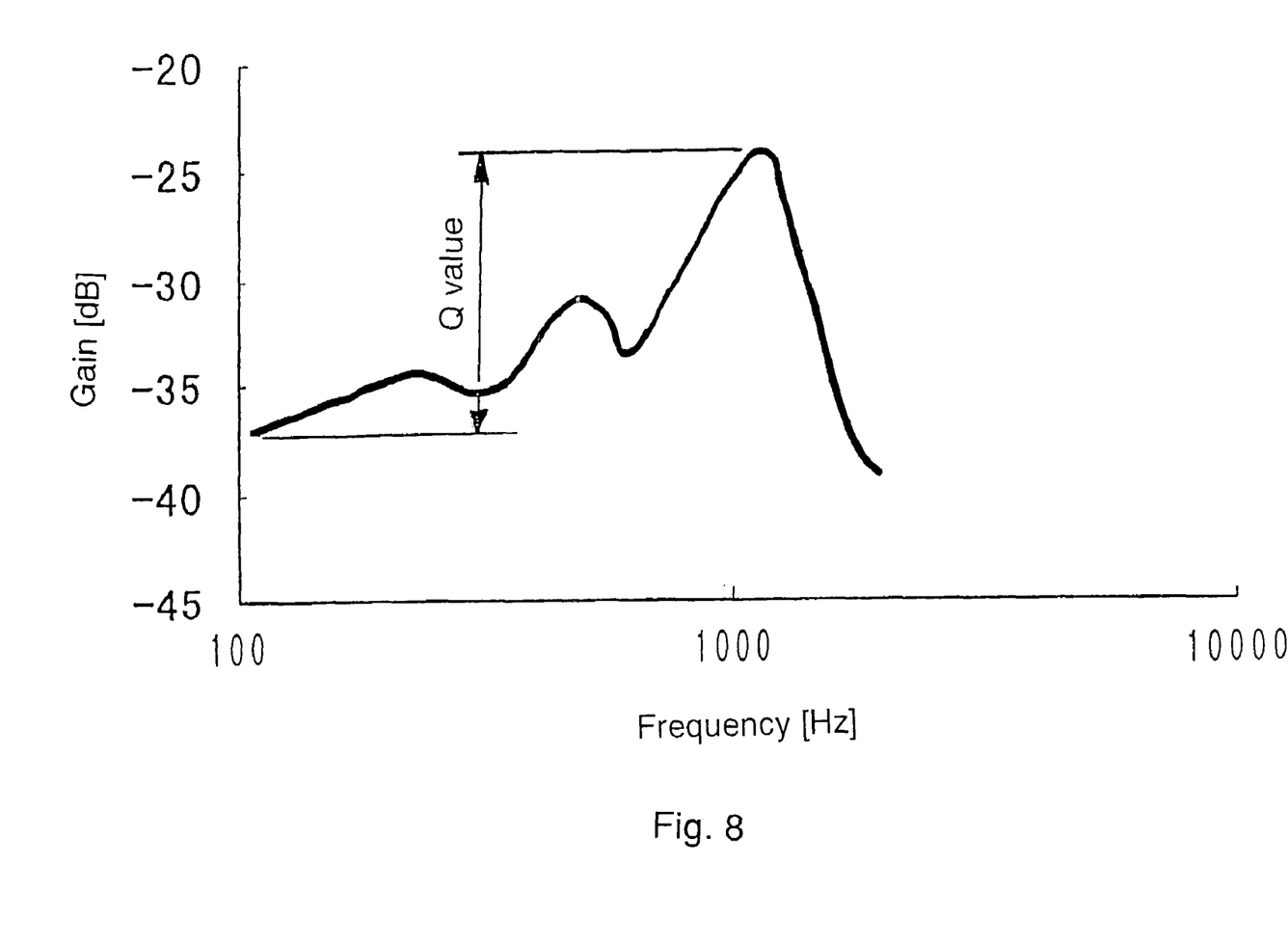
FIG. 8 shows an example of a result measured by the device of Example 3.

FIG. 8 shows the results obtained by measuring the Q value in this condition. The Q value is determined from a ratio between a gain at a frequency of 100 Hz and a gain at a peak. Note that, it is recognized that a Q value is slightly changed according to an amplitude of P (when P is made weak, the Q value becomes smaller). Accordingly, it is preferable that the Q value is appropriately corrected according to P.

INDUSTRIAL APPLICABILITY

According to the present invention, a person other than a doctor or a health professional can conduct safe measurement because the cornea is not directly stimulated. In addition, intraocular tension can be measured more easily and accurately because it is unnecessary to conduct correction according to the size of the eyeball.

What is claimed is:

1. A method for measuring intraocular tension of an eyeball in a mammal, comprising:
   vibrating the eyeball to be examined by vibrating the outside of an eyelid covering the eyeball of said mammal with said eyelid closed by a sound wave,
   noninvasively measuring vibration of the eyeball to be examined by measuring the vibration of the eyeball on the closed eyelid to determine a Q value of resonance of the eyeball, and
   calculating intraocular tension from the Q value.

2. The method of claim 1, additionally comprising adjusting the pressure so that the eyelid is slightly deformed, and the eyeball is kept in a natural state in which it is not deformed.

3. The method of claim 1, wherein the intraocular tension is calculated from the Q value based on a predetermined relationship between the intraocular tension and the Q value.

4. An intraocular tension measuring device comprising a vibrating means for vibrating an eyeball by a sound wave, a measuring means for noninvasively measuring vibration of the eyeball to be examined, a Q value calculating means for calculating a Q value of resonance of the eyeball to be examined from the vibration measured by the measuring means, and an intraocular tension calculating means for calculating intraocular tension from the Q value, wherein the vibrating means and the measuring means are adapted to be located on an eyelid of the eyeball.

5. The intraocular tension measuring device according to claim 4, wherein the vibrating means and the measuring means are attached to a main body so that the vibrating means and the measuring means can be located on the eyelid, and wherein the main body is inserted into a holder so that the main body can be moved in the axis direction of the holder.

* * * * *